(12) United States Patent
Andrews et al.

(10) Patent No.: US 8,207,202 B2
(45) Date of Patent: Jun. 26, 2012

(54) BENZAMIDE COMPOUNDS USEFUL AS HISTONE DEACETYLASE INHIBITORS

(75) Inventors: David Michael Andrews, Macclesfield (GB); Elaine Sophie Elizabeth Stokes, Macclesfield (GB); Andrew Turner, Macclesfield (GB); Michael James Waring, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 1048 days.

(21) Appl. No.: 12/090,611

(22) PCT Filed: Oct. 17, 2006

(86) PCT No.: PCT/GB2006/003838
§ 371 (c)(1),
(2), (4) Date: Apr. 17, 2008

(87) PCT Pub. No.: WO2007/045844
PCT Pub. Date: Apr. 26, 2007

(65) Prior Publication Data
US 2008/0269294 A1    Oct. 30, 2008

(30) Foreign Application Priority Data

Oct. 19, 2005  (GB) .................................. 0521244.4

(51) Int. Cl.
*A61K 31/454* (2006.01)
*C07D 401/06* (2006.01)

(52) U.S. Cl. ........................................ 514/326; 546/210
(58) Field of Classification Search .................. 514/326; 546/210
See application file for complete search history.

(56) References Cited

U.S. PATENT DOCUMENTS

| | | | |
|---|---|---|---|
| 3,931,215 A | 1/1976 | Horn et al. | |
| 3,974,172 A | 8/1976 | Sahm et al. | |
| 4,289,887 A | 9/1981 | Wehling | |
| 5,232,937 A | 8/1993 | Makovec et al. | |
| 2002/0091116 A1 | 7/2002 | Zhu et al. | |
| 2005/0124497 A1 | 6/2005 | Fusslein et al. | |

FOREIGN PATENT DOCUMENTS

| | | |
|---|---|---|
| EP | 1273575 B1 | 1/2003 |
| JP | 05-239069 A | 9/1993 |
| JP | 11302173 A | 11/1999 |
| JP | 2000-302765 A | 10/2000 |
| WO | 0119798 A2 | 3/2001 |
| WO | 0138322 A1 | 5/2001 |
| WO | 0174791 A1 | 11/2001 |
| WO | 02051831 A1 | 7/2002 |
| WO | 03024448 A2 | 3/2003 |
| WO | 03087057 A1 | 10/2003 |
| WO | 03092686 A1 | 11/2003 |
| WO | 2004005513 A2 | 1/2004 |
| WO | 2004085385 A2 | 10/2004 |
| WO | 2005030704 A1 | 4/2005 |
| WO | 2005030705 A1 | 4/2005 |
| WO | 2005092899 A1 | 10/2005 |
| WO | 2006024841 A2 | 3/2006 |
| WO | 2006064246 A1 | 6/2006 |
| WO | 2006075160 A1 | 7/2006 |
| WO | 2006077387 A2 | 7/2006 |
| WO | 2007071956 A1 | 6/2007 |
| WO | 2007071961 A1 | 6/2007 |

OTHER PUBLICATIONS

Lima et al. "Bioisosterim . . . " Current Med. Chem. v.12 p. 23-49 (2005).*
David M. Andrews. Oral small molecule anticancer lead optimization: Lessons in campaign design, synthesis and testing, 236th ACS National Meeting, Philadelphia, PA, Aug. 17-21, 2008, (Lecture given on Aug. 21st).
Koshio, H. "Preparation of phenyldiazepane derivatives or salt thereof having anticoagulant activity", Chemical Abstracts Online, database accession No. 133:321906, (2000).
Yamada, Y et al: "Preparation of benzothiazole and benzoxazole derivatives and analogs as liquid crystals", Chemical Abstract online, database accession No. 121:122228, (1994).
Andrews A.M. et al: "Design and Campaign Synthesis of piperidine- and thiazole-based histone deacetylase inhibitors", Bioorganic and Medicinal Chemistry Letters, 2008, 18, 2580-2584.
Andrews A.M. et al: "Design and Campaign Synthesis of pyridine-based histone deacetylase inhibitors", Bioorganic and Medicinal Chemistry Letters, 2008, 18, 2525-2529.
Final rejection from US PTO for U.S. Appl. No. 10/509,941 (corresponds to WO 03/087057 A),(2007).
Response to US Office Action dated Sep. 10, 2007 for U.S. Appl. No. 10/509,941 (corresponds to WO 03/087057 A). Includes current US claim set.

* cited by examiner

*Primary Examiner* — Celia Chang
(74) *Attorney, Agent, or Firm* — Astrazeneca AB

(57) ABSTRACT

The invention concerns benzamide compounds of formula (I), wherein $R^1$ is a C-linked pyrazole ring, which is optionally substituted by one or more groups selected from $C_{1-4}$alkyl, $C_{3-4}$cycloalkyl, $C_{1-4}$alkoxy and $C_{3-4}$cycloalkoxy; or a pharmaceutically acceptable salt or pro-drug form thereof. The invention also concerns processes for the preparation of such compounds, pharmaceutical compositions containing them and their use in the manufacture of a medicament for use as an antiproliferative agent in the prevention or treatment of tumors or other proliferative conditions, which are sensitive to the inhibition of histone deacetylase (HDAC).

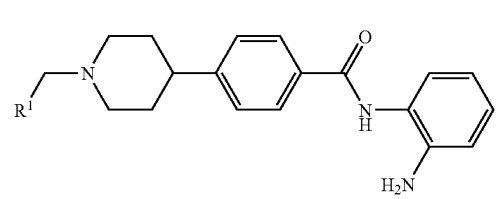

(I)

8 Claims, No Drawings

BENZAMIDE COMPOUNDS USEFUL AS HISTONE DEACETYLASE INHIBITORS

CROSS-REFERENCE TO RELATED APPLICATIONS

This application is a US National Stage under 35 U.S.C §371 of International Application No. PCT/GB2006/003838 (filed 17 Oct. 2006) which claims priority under 35 U.S.C. §119(a)-(d) to Great Britain Application No. GB 0521244.4 filed on 19 Oct. 2005.

This invention concerns certain novel benzamide compounds, or pharmaceutically acceptable salts thereof, which are potent inhibitors of the enzyme histone deacetylase (HDAC). The invention also relates to processes for the manufacture of these novel benzamide compounds, to pharmaceutical compositions containing them and to their use in therapeutic methods, for example in the manufacture of medicaments to inhibit HDAC in a warm-blooded animal, such as man.

HDAC activity has been associated with a number of disease states, such as cancer (Marks et al., Nature Reviews, 1, 194-202, (2001)), cystic fibrosis (Li, S. et al, J. Biol. Chem., 274, 7803-7815, (1999)), Huntingdons chorea (Steffan, J. S. et al., Nature, 413, 739-743, (2001)) and sickle cell anaemia (Gabbianelli, M. et al., Blood, 95, 3555-3561, (2000)). Accordingly, the invention also extends to methods of treating any of the aforementioned diseases using the benzamide compounds of the present invention, as well as to the use of these benzamide compounds in the manufacture of a medicament for the treatment of these disease states.

In the eukaryotic cell, DNA is routinely compacted to prevent transcription factor accessibility. When the cell is activated this compacted DNA is made available to DNA-binding proteins, thereby allowing the induction of gene transcription (Beato, M., J. Med. Chem., 74, 711-724 (1996); Wolffe, A. P., Nature, 387, 16-17 (1997)). Nuclear DNA associates with nuclear proteins known as histones to form a complex called chromatin. The core histones, termed H2A, H2B, H3 and H4, are surrounded by 146 base pairs of DNA to form the fundamental unit of chromatin, and which is known as the nucleosome. The N-terminal tails of the core histones contain lysine residues that are sites for post-transcriptional acetylation. Acetylation of the terminal amino group on the lysine side chain neutralizes the potential of the side chain to form a positive charge, and is thought to impact on chromatin structure.

Histone Deacetylases (HDACs) are zinc-containing enzymes which catalyse the removal of acetyl groups from the ε-amino termini of lysine residues clustered near the amino terminus of nucleosomal histones. HDACs may be divided into two classes, the first (HDAC 1, 2, 3 and 8) represented by yeast Rpd3-like proteins, and the second (HDAC 4, 5, 6, 7, 9 and 10) represented by yeast Hda1-like proteins. The reversible process of acetylation is known to be important in transcriptional regulation and cell-cycle progression. In addition, HDAC deregulation has been associated with several cancers and HDAC inhibitors, such as Trichostatin A (a natural product isolated from *Streptomyces hygroscopicus*), have been shown to exhibit significant cell growth inhibition and anti-tumour effects (Meinke, P. T., Current Medicinal Chemistry, 8, 211-235 (2001)). Yoshida et al, (*Exper. Cell Res.*, 177, 122-131 (1988)) teach that Trichostatin A causes the arrest of rat fibroblasts at the G1 and G2 phases of the cell cycle, thereby implicating the role of HDAC in the regulation of the cell cycle. Furthermore, Trichostatin A has been shown to induce terminal differentiation, inhibit cell growth, and prevent the formation of tumours in mice (Finnin et al., Nature, 401, 188-193 (1999)).

It is known from the published International Patent Application Numbers WO 03/087057 and WO 03/092686 that certain benzamide derivatives are inhibitors of HDAC. One particular compound disclosed in WO 03/087057 is N-(2-aminophenyl)-4-[1-(pyrid-2-ylmethyl)piperidin-4-yl]benzamide [1] (the structure of which is shown below).

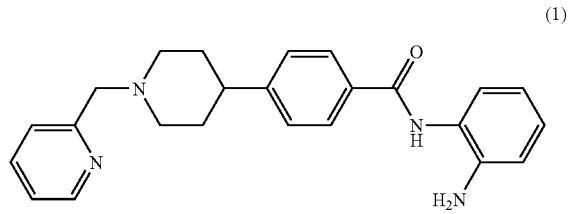

(1)

It has now been found that certain benzamide derivatives that bear an optionally substituted pyrazole group instead of the pyridyl group are potent inhibitors of HDAC. In addition, particular compounds of the present invention have also been found to possess other favourable pharmaceutical properties, including advantageous cell or in-vivo potency, advantageous DMPK properties (for example, a favourable bioavailability profile and/or favourable free-plasma levels and/or a favourable half life and/or a favourable volume of distribution), as well as good or enhanced solubility. In addition, the benzamide derivatives of the present invention generally show a particularly low activity in a hERG-encoded Potassium Channel Inhibition Assay, which is an indicator of undesirable and serious cardiovascular side effects in the clinic.

According to the present invention there is provided a compound of formula (I):

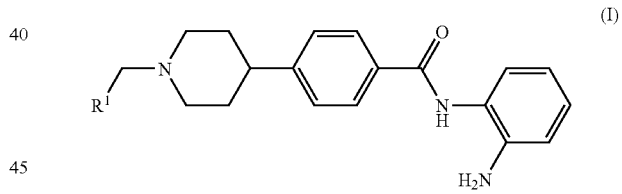

(I)

wherein $R^1$ is a carbon-linked pyrazole ring, which is optionally substituted by one or more groups selected from $C_{1-4}$alkyl, $C_{3-4}$cycloalkyl, $C_{1-4}$alkoxy and $C_{3-4}$cycloalkoxy; or a pharmaceutically acceptable salt thereof.

It is to be understood that certain compounds of Formula (I) defined above may exhibit the phenomenon of tautomerism. It is to be understood that the present invention includes in its definition any such tautomeric form, or a mixture thereof, which possesses the above-mentioned activity, and is not to be limited merely to any one tautomeric form utilised within the formulae drawings or named in the Examples.

Where optional substituents are selected from "one or more" substituent groups it is to be understood that this definition includes all substituents being chosen from one of the specified groups or the substituents being chosen from two or more of the specified groups.

Suitable optional substituents for $R^1$ may be present on any available carbon or nitrogen atoms within the pyrazole ring.

$R^1$ suitably carries from 1 to 3 substituent groups. Alternatively, $R^1$ is unsubstituted.

As used herein, the term "alkyl" refers to straight or branched chains. The term "cycloalkyl" includes ring structures, but may additionally include chains in the form of cycloalkyl-alkyl groups. By analogy, the terms "alkoxy" and "cycloalkoxy" comprise alkyl, cycloalkyl or cycloalkyl-alkyl groups linked through an oxygen atom.

Suitable $C_{1-4}$alkyl or $C_{3-4}$cycloalkyl substituents for $R^1$ include methyl, ethyl, propyl, cyclopropyl, cyclobutyl, or cyclopropylmethyl.

Suitable $C_{1-4}$alkoxy and $C_{3-4}$cycloalkoxy substituents for $R^1$ include methoxy, ethoxy, propoxy, cyclopropoxy, cyclobutoxy, or methylcyclopropoxy.

In a particular embodiment of the invention, $R^1$ is a carbon-linked pyrazole ring, which is optionally substituted by 1, 2 or 3 groups selected from $C_{1-4}$alkyl or $C_{1-4}$alkoxy.

In a further embodiment of the invention, $R^1$ is a carbon-linked pyrazole ring, which is optionally substituted by 1, 2 or 3 groups selected from $C_{1-2}$alkyl or $C_{1-2}$alkoxy.

Examples of $R^1$ groups include pyrazol-3-yl, pyrazol-4-yl, 1-methylpyrazol-4-yl, 3-ethylpyrazol-4-yl, 1,3-dimethylpyrazol-5-yl, 1,3-dimethylpyrazol-4-yl, 1,3,5-trimethylpyrazol-4-yl, 1,3-dimethyl-5-methoxypyrazol-4-yl, 1,5-dimethylpyrazol-4-yl, 1-ethyl-5-methylpyrazol-4-yl, 1-ethylpyrazol-4-yl, and 1-ethyl-3-methylpyrazol-4-yl (subject to tautomerism where possible).

In a further embodiment of the invention, compounds of formula (I) comprise compounds of formula (IA)

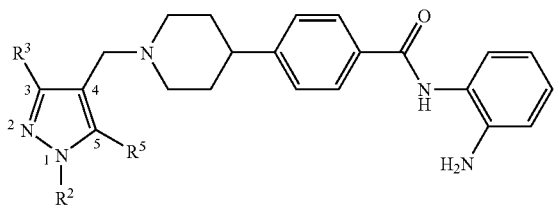

(IA)

where $R^2$ is hydrogen, $C_{1-4}$alkyl or $C_{3-4}$cycloalkyl, and $R^3$ and $R^5$ are independently selected from hydrogen, $C_{1-4}$alkyl, $C_{3-4}$cycloalkyl, $C_{1-4}$alkoxy or $C_{3-4}$cycloalkoxy.

It will be appreciated that the ring atoms of the pyrazole portion of the molecule of formula (IA) are generally numbered as shown in the diagram above. However, the molecule is subject to tautomerism in the case where $R^2$ is hydrogen, where the switching of hydrogen groups from one nitrogen of the pyrazole ring to the other, means that substituted pyrazoles, where at least one of $R^3$ or $R^5$ is other than hydrogen, are inevitably mixtures of each tautomer, and that $R^3$ and $R^5$ are therefore deemed to be interchangeable.

In an alternative embodiment, the invention provides a compound of formula (IB)

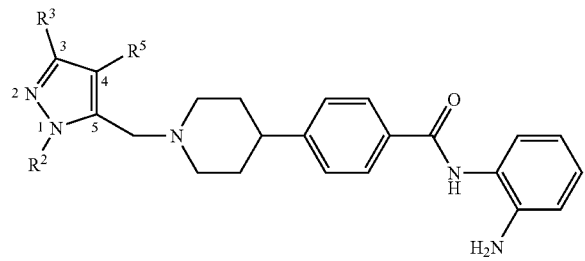

(IB)

where $R^2$, $R^3$ and $R^5$ are as defined above in relation to formula (IA)

Again, it will be appreciated that the pyrazole portion of the molecule of formula (IB) is generally numbered according to that delineated in the diagram above. However, as for the compounds of formula (IA) discussed above, the molecule is also subject to tautomerism when $R^2$ is hydrogen.

Particular examples $R^2$ include hydrogen, methyl, ethyl, propyl, cyclopropyl, methylcyclopropyl or cyclobutyl.

For instance, $R^1$ is hydrogen, methyl, ethyl, propyl or cyclopropyl.

In a particular embodiment, $R^2$ is hydrogen, methyl or ethyl.

In a further embodiment, $R^2$ is hydrogen or methyl.

Particular examples of groups $R^3$ and $R^5$ are hydrogen methyl, ethyl, propyl, cyclopropyl, cyclopropylmethyl, methoxy, ethoxy, propoxy or cyclopropoxy.

Particular examples of groups $R^3$ or $R^5$ include hydrogen, methyl, ethyl or methoxy.

Suitably, no more than one group $R^3$ or $R^5$ is a $C_{1-4}$alkoxy.

In a particular embodiment, at least one, and preferably two groups $R^2$, $R^3$ and $R^5$ are other than hydrogen.

In a particular embodiment of the invention, the compounds have the structural formula (IA) shown above wherein $R^2$ is hydrogen or $C_{1-4}$alkyl, and $R^3$ and $R^5$ are each independently selected from hydrogen, $C_{1-4}$alkyl, or $C_{1-4}$alkoxy.

In a further embodiment, the compounds have the structural formula (IA) shown above wherein $R^2$ is hydrogen, methyl or ethyl, and $R^3$ and $R^5$ are each independently selected from hydrogen, methyl, ethyl or methoxy.

In a further embodiment, the compounds have the structural formula (IA) shown above wherein $R^2$ is hydrogen or methyl, and $R^3$ and $R^5$ are each independently selected from hydrogen, methyl, ethyl or methoxy.

In a further embodiment, the compounds have the structural formula (IA) shown above wherein $R^2$ is hydrogen or methyl, and $R^3$ and $R^5$ are each independently selected from hydrogen, methyl or methoxy.

In a further embodiment, the compounds have the structural formula (IA) shown above wherein $R^2$ is hydrogen or methyl, and $R^3$ and $R^5$ are each independently selected from hydrogen or methyl.

In a particular embodiment of the invention, the compounds have the structural formula (IB) shown above wherein $R^2$ is hydrogen or $C_{1-4}$alkyl, and $R^3$ and $R^5$ are each independently selected from hydrogen, $C_{1-4}$alkyl, or $C_{1-4}$alkoxy.

In a further embodiment, the compounds have the structural formula (IB) shown above wherein $R^2$ is hydrogen, methyl or ethyl, and $R^3$ and $R^5$ are each independently selected from hydrogen, methyl, ethyl or methoxy.

In a further embodiment, the compounds have the structural formula (IB) shown above wherein $R^2$ is hydrogen or methyl, and $R^3$ and $R^5$ are each independently selected from hydrogen, methyl, ethyl or methoxy.

In a further embodiment, the compounds have the structural formula (IB) shown above wherein $R^2$ is hydrogen or methyl, and $R^3$ and $R^5$ are each independently selected from hydrogen, methyl or methoxy.

Particular compounds of the invention include any one of the following:
N-(2-aminophenyl)-4-[1-(1H-pyrazol-3-ylmethyl)piperidin-4-yl]benzamide;
N-(2-aminophenyl)-4-{1-[(5-methoxy-1,3-dimethyl-1H-pyrazol-4-yl)methyl]piperidin-4-yl}benzamide;
N-(2-aminophenyl)-4-{1-[(3-ethyl-1H-pyrazol-4-yl)methyl]piperidin-4-yl}benzamide;
N-(2-aminophenyl)-4-{1-[(1-methyl-1H-pyrazol-4-yl)methyl]piperidin-4-yl}benzamide;

N-(2-aminophenyl)-4-{1-[(1,3-dimethyl-1H-pyrazol-5-yl)methyl]piperidin-4-yl}benzamide;

N-(2-aminophenyl)-4-{1-[(1,3-dimethyl-1H-pyrazol-4-yl)methyl]piperidin-4-yl}benzamide;

N-(2-aminophenyl)-4-{1-[(1,3,5-trimethyl-1H-pyrazol-4-yl)methyl]piperidin-4-yl}benzamide;

N-(2-aminophenyl)-4-{1-[(1,5-dimethyl-1H-pyrazol-4-yl)methyl]piperidin-4-yl}benzamide;

N-(2-aminophenyl)-4-{1-[(1-ethyl-5-methyl-1H-pyrazol-4-yl)methyl]piperidin-4-yl}benzamide;

N-(2-aminophenyl)-4-{1-[(1-ethyl-1H-pyrazol-4-yl)methyl]piperidin-4-yl}benzamide;

N-(2-aminophenyl)-4-{1-[(1-ethyl-3-methyl-1H-pyrazol-4-yl)methyl]piperidin-4-yl}benzamide;

or a pharmaceutically acceptable salt thereof.

It is to be understood that certain compounds of Formula I above may exist in unsolvated forms as well as solvated forms, such as, for example, hydrated forms. It is to be understood that the present invention encompasses all such solvated forms that possess antiproliferative activity.

It is also to be understood that certain compounds of the Formula I may exhibit polymorphism, and that the present invention encompasses all such forms which possess antiproliferative activity.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt. A further suitable pharmaceutically-acceptable salt of a compound of the Formula I is, for example, a salt formed within the human or animal body after administration of a compound of the Formula I.

The compounds of the invention may be administered in the form of a pro-drug—that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable amide derivatives that may be formed at an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I is, for example, an in vivo cleavable amide derivative thereof. Suitable pharmaceutically-acceptable amides formed from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Preparation of Compounds of Formula I

It will be appreciated by a person skilled in the art that it may be necessary/desirable to protect any sensitive groups in the compounds in some of the processes/reactions mentioned herein. The instances where protection is necessary or desirable, and suitable methods for providing such protection are known to those skilled in the art. Conventional protecting groups may be used in accordance with standard practice (for illustration see T. W. Green & P. G. M. Wuts, Protective Groups in Organic Synthesis, 3$^{rd}$ edition, John Wiley and Sons, 1999). Thus, if reactants include groups such as amino, carboxy or hydroxy it may be desirable to protect the group in some of the reactions mentioned herein.

Any protecting groups utilised in the processes described herein may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In a further aspect, the present invention provides a process for preparing a compound of formula (I) or a pharmaceutically acceptable salt thereof, which process comprises:
(a) reaction of a compound of formula (II)

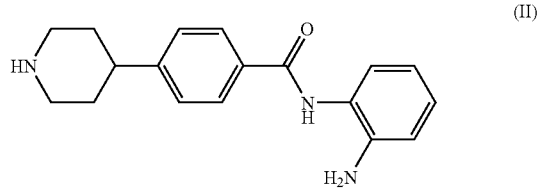

wherein the aniline moiety may be appropriately protected; with a compound of the formula (III)

$$R^1CHO \qquad (III)$$

where $R^1$ is as defined herein, in the presence of a reducing agent, and thereafter, if necessary, removing any residual protecting groups that may be present.

A suitable reducing agent is for process (a) includes, for example, an inorganic borohydride salt such as sodium borohydride, sodium triacetoxyborohydride or sodium cyanoborohydride and hydrogen. Reductive amination using hydrogen is optionally carried out in the presence of a suitable catalyst, such as, for example, Pd/C, Pd(OH)$_2$/C, Pt/C, PtO$_2$ or Rh on alumina, and may also be carried out under pressure, for example 1-10 bar over a range of temperatures, for example 0-150° C.

Process (a) may be carried out in the presence of a suitable acid. A suitable acid for process (a), includes a Bronsted acid such as, for example formic acid, acetic acid, trifluoroacetic acid, hydrochloric acid, sulphuric acid, paratoluene sulfonic acid or camphor sulfonic acid; or a Lewis acid of formula MQ$_z$, wherein M is a metal, Q is a reactive group such as, for example, a halo or a sulphonyloxy group, for example a chloro, bromo, iodo, methanesulphonyloxy, trifluoromethanesulphonyloxy or toluene-4-sulphonyloxy group, and z is in the range of 1-6 and the value of z will depend on the metal M. Typical examples of suitable Lewis acids include boron trifluoride, scandium(III) trifluoromethanesulfonate, tin(VI) chloride, titanium(IV) isopropoxide or zinc (II) chloride.

Alternatively, the compounds of formula (I) may be prepared by
(b) reaction of a compound of formula (II),

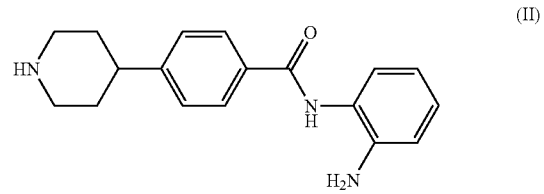

wherein the aniline may be appropriately protected; with a compound of the formula (IV)

$$R^1CH_2X \qquad (IV)$$

in the presence of a suitable base;
wherein X is a reactive group;
and thereafter, if necessary, removing any residual protecting groups that may be present.

A suitable reactive group X is, for example, a halogeno or sulphonyloxy group, for example a chloro, bromo, iodo, methanesulphonyloxy, trifluoromethanesulphonyloxy or toluene-4-sulphonyloxy group.

A suitable base for use in process (b) above is, for example, an organic amine base such as, for example, pyridine, 2,6-lutidine, collidine, 4-dimethylaminopyridine, triethylamine, morpholine, diisopropylethylamine (DIPEA), N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride, an alkaline earth metal hydrogencarbonate such as sodium hydrogencarbonate, or a metal alkoxide such as sodium ethoxide.

A suitable protecting group for the aniline moiety or the piperidine ring may be a carbamate such as tert-butoxycarbonyl or benzyloxycarbonyl.

Particular examples of groups $R^1$ are as described above.

The reactions defined in processes (a) and (b) are conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran, 1,2-dimethoxyethane or 1,4-dioxan, an aromatic solvent such as toluene, or a dipolar aprotic solvent such as N,N-dimethylformamide, N N-dimethylacetamide, N-methylpyrrolidin-2-one or dimethylsulphoxide.

Preparation of Starting Materials

Preparation of the Compound of Formula II

The compound of Formula II above may be prepared by either of the following processes:

(c) The reaction of a compound of the formula (V), wherein the aniline may be appropriately protected,

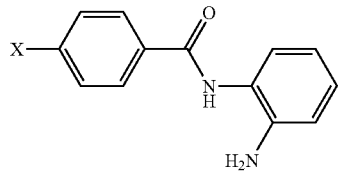

(V)

wherein X is a reactive group as defined hereinbefore, with a compound of the formula (VI) in the presence of a suitable base

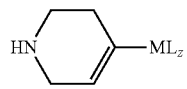

(VI)

wherein M is a metal, L is a ligand, integer z is 0 to 3, and the tetrahydropyridine ring may be protected; or the reaction of a compound of the formula (VII), wherein the aniline and the tetrahydropyridine may be appropriately protected and M, L and z are as defined above,

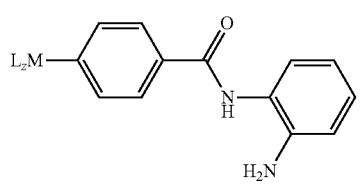

(VII)

with a compound of Formula (VIII):

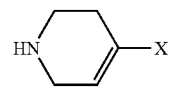

(VIII)

in the presence of a suitable base;
wherein X is a reactive group as defined hereinbefore,
and thereafter, if necessary, and in any suitable order or combination:
removing any protecting groups from the tetrahydropyridine, and/or
reduction of the tetrahydropyridine to piperidine and/or removing any residual protecting groups present.

A suitable protecting group for the tetrahydropyridine ring is a group such as tert-butoxycarbonyl (also referred to herein as "BOC") or benzyloxycarbonyl. A suitable protecting group for the aniline moiety may also be a carbamate such as BOC or benzyloxycarbonyl.

A suitable base for process (c) is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, cesium carbonate, sodium hydroxide or potassium hydroxide, or, for example, an alkali metal hydride, for example sodium hydride, or an alkaline metal hydrogencarbonate such as sodium hydrogencarbonate, or a metal alkoxide such as sodium ethoxide.

The reaction defined in process (c) above is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran, 1,2-dimethoxyethane or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reactions are conveniently carried out at a temperature in the range, for example, 10 to 250° C., preferably in the range 40 to 80° C.;

Metal M may be any metal that is known in the literature to form organometallic compounds that undergo catalytic cross coupling reactions. Examples of suitable metals include boron, tin, zinc, and magnesium.

A suitable value for integer z is dependent on the metal M, but is usually in the range 0-3.

Suitable values for the ligand L, when present, include, for example, a hydroxy, a halo, (1-4C)alkoxy or (1-6C)alkyl ligand, for example a hydroxy, bromo, chloro, fluoro, iodo, methoxy, ethoxy, propoxy, isopropoxy, butoxy, methyl, ethyl, propyl, isopropyl or butyl ligand or, where integer z is 2 and M is boron, the two ligands present may be linked such that, together with the boron atom to which they are attached, they form a ring. Suitably, the group $ML_z$ is a group of the formula —$BL^1L^2$, where B is boron and $L^1$ and $L^2$ are as defined for ligand L above. In particular, the ligands $L^1$ and $L^2$ may be linked such that, together with the boron atom to which they are attached, they form a ring. For example, $L^1$ and $L^2$ may together define an oxy-(2-4C)alkylene-oxy group, for example an oxyethyleneoxy, pinacolato (—O—C(CH$_3$)$_2$C(CH$_3$)$_2$—O—) or oxypropyleneoxy group such that, together with the boron atom to which they are attached, they form a cyclic boronic acid ester group.

A suitable catalyst for process (c) includes, for example, a metallic catalyst such as a palladium(0), palladium(II), nickel (0) or nickel(II) catalyst, for example tetrakis(triphenylphosphine)palladium(0), palladium(II) chloride, palladium(II) bromide, bis(triphenylphosphine)palladium(II) chloride, tetrakis(triphenylphosphine)nickel(0), nickel(II) chloride, nickel(II) bromide, bis(triphenylphosphine)nickel(II) chloride or dichloro[1-1'-bis(diphenylphosphino)ferrocene]palladium (II). In addition, a free radical initiator may conveniently be added, for example an azo compound such as azo(bisisobutyronitrile).

Suitably the tetrahydropyridine ring is reduced to a piperidine ring in process (c) above by hydrogenation. Hydrogenation is optionally carried out in the presence of a suitable catalyst, such as, for example, Pd/C, Pd(OH)$_2$/C, Pt/C, PtO$_2$ or Rh on alumina, and may also be carried out under pressure, for example 1-10 bar. Hydrogenation is also suitably carried out in the presence a suitable acid, for example hydrobromic acid, hydrochloric acid, citric acid, acetic acid and methanesulphonic acid, and in an appropriate solvent or solvent mixture such as, for example, water, ethanol, tetrahydrofuran (THF), methanol, acetonitrile or propan-2-ol.

d) The reaction of a compound of formula (IX), wherein Q$_1$ is —OH, —Cl, or —O$^-$ Q$_2^+$ (wherein Q$_2^+$ is a cation)

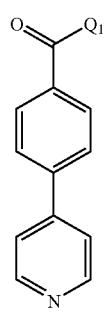

(IX)

with a compound of formula (X) in the presence of a suitable solvent and wherein one of the amino groups in the compound of formula (X) may be protected;

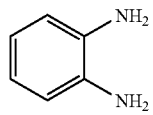

(X)

to form a compound of formula (XI)

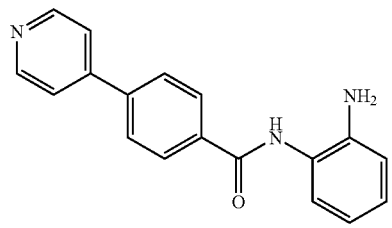

(XI)

wherein the aniline may be protected;

and thereafter:
converting the compound of formula (XI) to a compound of formula (II) by reducing the pyrindin-4-yl ring to a piperidine-4-yl ring using a suitable reducing agent and/or suitable reducing conditions; and
optionally removing any residual protecting groups present.

A suitable value for Q$_1$ is —O$^-$Na$^+$ (i.e. –O$^-$ Q$_2^+$, wherein Q$_2^+$ is Na). Suitably, one of the amino groups of the compound of formula (X) is protected by a suitable amino protecting group as hereinbefore defined, such as a BOC group.

Suitably, the aniline is protected by an amino protecting group as hereinbefore defined, such as a BOC group, in the compound of formula (XI).

Any suitable solvent, such as those previously mentioned herein, may be used for the reaction of compounds I× and X.

The compound of formula (XI) is converted to into a compound of formula (II) using a suitable reducing agent and/or suitable reducing conditions. A suitable process is hydrogenation. Hydrogenation is optionally carried out in the presence of a suitable catalyst, such as, for example, Pd/C, Pd(OH)$_2$/C, Pt/C, PtO$_2$ or Rh on alumina, and may also be carried out under pressure, for example 1-10 bar. Hydrogenation is also suitably carried out in the presence a suitable acid, for example hydrobromic acid, hydrochloric acid, citric acid, acetic acid and methanesulphonic acid, and in an appropriate solvent or solvent mixture such as, for example, water, ethanol, tetrahydrofuran (THF), methanol, acetonitrile or propan-2-ol.

A suitable method for preparation of the compound formula (XI) comprises the conversion of the compound (IX) into a reactive derivative of the carboxylic acid (which may be produced in situ and is not necessarily isolated), followed by subsequent reaction with a compound of formula (X).

A suitable reactive derivative of a carboxylic acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester; the product of the reaction of the acid and a carbodiimide such as dicyclohexylcarbodiimide; or the product of the reaction of an acid with 4-(4,6-dimethoxy-1,3,5-triazinyl-2-yl)-4-methylmorpholinium chloride (DMTMM), or the product of the reaction of an acid with 1,1'-carbonyldiimidazole (CDI).

Compounds of formulae (III) and (IV) are either obtainable from commercial sources, for example Fluorochem Ltd, Old Glossop, Derbyshire SK13 7RY, UK, or they may be synthesised using methods which are known to those skilled in the art and/or reported in the literature, for example Makino, K.; Kim, H. S and Kurasawa Y; J. Heterocyclic Chem. 1998, 35, 489-497 and references therein.

Assays

The following assays (a) to (c) can be used to measure the effects of one or more of the compounds of the present invention as HDAC inhibitors, as inhibitors in vitro of recombinant human HDAC1 produced in Hi5 insect cells, and as inducers in vitro & in vivo of Histone H3 acetylation in whole cells and tumours. They also assess the ability of such compounds to inhibit proliferation of human tumour cells.

(a) In Vitro Enzyme Assay of recombinant HDAC1

HDAC inhibitors were screened against recombinant human HDAC1 produced in Hi5 insect cells. The enzyme was cloned with a FLAG tag at the C-terminal of the gene and affinity purified using Anti-FLAG M2 agarose from SIGMA (A2220).

The deacetylase assays were carried out in a 50 µl reaction. HDAC1 (75 ng of enzyme) diluted in 15 µl of reaction buffer (25 mM Tris HCl (pH 8), 137 mM NaCl, 2.7 mM KCl, 1 mM MgCl$_2$) was mixed with either buffer alone (10 µl) or buffer containing compound (10 µl) for 30 minutes at ambient temperature. 25 µM acetylated histone H4 peptide (KI 174 Biomol) diluted in 25 µl of buffer was then added to the reaction and incubated for one hour at ambient temperature. The reaction was stopped by addition of an equal volume (50 µl) of Fluor de Lys developer (Biomol) containing Trichostatin A at 2 µM. The reaction was allowed to develop for 30 minutes at ambient temperature and then fluorescence measured at an excitation wavelength of 360 nM and an emission wavelength of 465 nM. IC$_{50}$ values for HDAC enzyme inhibitors were determined by performing dose response curves with individual compounds and determining the concentration of inhibitor producing fifty percent decrease in the maximal signal (diluent control).

(b) In Vitro Assay of Inhibition of Proliferation in Whole Cells

Inhibition of proliferation in whole cells was assayed using the Promega cell titer 96 aqueous proliferation assay (Promega #G5421). HCT116 cells were seeded in 96 well plates at 1×10$^3$ cells/well, and allowed to adhere overnight. They were treated with inhibitors for 72 hours. 20 µl of the tetrazolium dye MTS was added to each well and the plates were re-incubated for 3 hours. Absorbance was then measured on a 96 well plate reader at 490 nM. The IC$_{50}$ values for HDAC inhibitors were determined by performing dose response curves with individual compounds and determining the concentration of inhibitor producing fifty percent decrease in the maximal signal (diluent control).

(c) In Vitro Enzyme Assay of Histone Deacetylase activity in whole cells

Histone H3 acetylation in whole cells was measured using immunohistochemistry and analysis using the Cellomics arrayscan. A549 or HCT116 cells were seeded in 96 well plates at 1×10$^4$ cells/well, and allowed to adhere overnight. They were treated with inhibitors for 24 hours and then fixed in 1.8% formaldehyde in tris buffered saline (TBS) for one hour. Cells were permeabilized with ice-cold methanol for 5 minutes, rinsed in TBS and then blocked in TBS 3% low-fat dried milk for 90 minutes. Cells were then incubated with polyclonal antibodies specific for the acetylated histone H3 (Upstate #06-599) diluted 1 in 500 in TBS 3% milk for one hour. Cells were rinsed three times in TBS and then incubated with fluorescein conjugated secondary antibodies (Molecular Probes #A11008) & Hoechst 333542 (1 µg/ml) (Molecular Probes #H3570) in TBS plus 1% Bovine serum albumin (Sigma #B6917) for one hour. Unbound antibody was removed by three rinses with TBS and after the final rinse 100 µl of TBS was added to the cells and the plates sealed and analysed using the Cellomics arrayscan.

EC$_{50}$ values for HDAC inhibitors were determined by performing dose response curves with individual compounds and then determining the concentration of inhibitor producing fifty percent of the maximal signal (reference compound control-Trichostatin A (Sigma)).

The HERG activity and solubility of the compounds of the invention can also be evaluated using assays (d) to (f) set out below:

(d) hERG-Encoded Potassium Channel Inhibition Assay
Cell Culture

Chinese Hamster Ovary (CHO) cells expressing the hERG-encoded channel were grown to semi-confluence at 37° C. in a humidified environment (5% CO$_2$) in F-12 Ham medium containing L-glutamine, 10% Foetal Calf Serum (FCS) and 0.6 mg/ml Hygromycin (all Sigma). Prior to use the monolayer was washed using a pre-warmed (37° C.) 3 ml aliquot of Versene 1:5,000 (Invitrogen). After aspiration of this solution, the flask was incubated at 37° C. in an incubator with a further 2 ml of Versene 1:5,000 for a period of 6 minutes. Cells were then detached from the bottom of the flask by gentle tapping and 10 ml of Dulbecco's-PBS containing calcium (0.9 mM) and magnesium (0.5 mM) (PBS) (Invitrogen) was then added to the flask and aspirated into a 15 ml centrifuge tube prior to centrifugation (50 g, for 4 minutes).

The resulting supernatant was discarded and the pellet gently re-suspended in a 3 ml aliquot of PBS. A 0.5 ml aliquot of cell suspension was removed for automated cell counting (Innovatis Cedex) and the final cell suspension volume adjusted with PBS to give the desired final cell concentration.
Electrophysiology The principles and operation of this device have been described previously (Schroeder et al., Journal of Biomolecular Screening (2003) 8(1), 50-64). Briefly, the technology is based on a 384-well plate (PatchPlate™) in which a recording is attempted in each well by using suction to try to position and hold a cell on a small hole separating two isolated fluid chambers. Once sealing has taken place, the solution on the underside of the PatchPlate™ is changed to one containing the amphotericin B (Sigma). This permeablises the patch of cell membrane covering the hole in each well and in effect allows a perforated, whole-cell patch clamp recording to be attempted in each well.

For each run of IonWorks™ HT it was operated in the following way at room temperature (~21° C.). The "boat" in the "Buffer" position was loaded with 4 ml of PBS and that in the "Cells" position with the CHO-HERG cell suspension described above. A 96-well plate (V-bottom, Greiner Bio-one) containing the compounds to be tested (at 3× their final test concentration) was placed in the "Plate 1" position and a PatchPlate™ was placed in the device and held in position using the Patchplate™ cover.

Each compound plate was laid-out to enable ten, 8-point concentration effect-curves to be constructed; the remaining two columns on the plate were taken up with vehicle (0.33% DMSO), to define the assay baseline, and a supra-maximal blocking concentration of cisapride (10 µM), to define the 100% inhibition level. The Fluidics-head (F-Head) of IonWorks™ HT then added 3.5 µl of PBS to each well of the PatchPlate™ and its underside was perfused with "Internal" solution that had the following composition (in mM): K-Gluconate 100, KCl 40, MgCl$_2$ 3.2, EGTA 3 and HEPES 5 (all Sigma) (pH 7.25-7.30 using 10 M KOH). After priming and de-bubbling, the Electronics-head (E-head) then moved round the PatchPlate™ to do a hole test (i.e. apply a voltage pulse to determine whether the hole in each well was open). The F-head then dispensed 3.5 µl of the cell suspension described above into each well of the PatchPlate™ and the cells were given 200 seconds to reach and seal to the hole in each well. The E-head then moved round the PatchPlate™ to determine the seal resistance obtained in each well.

The solution on the underside of the PatchPlate™ was then changed to "Access" solution that had the following composition (in mM): KCl 140, EGTA 1, MgCl$_2$ 1 and HEPES 20 (all Sigma) (pH 7.25-7.30 using 10 M KOH) plus 100 µg/ml of amphotericin B. After 9 minutes to allow patch perforation to take place, the E-head then moved around all 384 wells of the patch plate to obtain pre-compound hERG current measurements. The F-head then added 3.5 µl of solution from each well of the compound plate to 4 wells on the PatchPlate™. It was programmed to start with the most dilute well on the compound plate and move to the most concentrated well to minimise the impact of any carry-over issues.

After approximately three and a half minutes incubation, the E-head then moved around all 384-wells of the Patch-Plate™ to obtain post-compound HERG current measurements. In this way, non-cumulative concentration-effect curves could be produced where, providing the acceptance criteria were achieved in a sufficient percentage of wells (see below), the effect of each concentration of test compound was based on recording from between 1 and 4 cells.

The acceptance criteria for each well were: pre-scan seal resistance>60 MΩ, pre-scan HERG tail current amplitude>0.15 nA; post-scan seal resistance>60 MΩ. The pre- and post-compound hERG current was evoked by a voltage pulse consisting of a 20 s period holding at −70 mV, a 160 ms step to −60 mV, a 100 ms step back to −70 mV, a 1 s step to +40 mV, a 2 s step to −30 mV and finally a 500 ms step to −70 mV. In between the pre- and post-compound voltage pulses there was no clamping of the membrane potential.

e) Assessment of Aqueous Solubility.

Test compound (from 1 to 1.6 mgs) is weighed into a vial and 1 ml of 0.1 M phosphate buffer (pH 7.4) is added. Between 1.0 and 1.6 mgs of test compound is concurrently dissolved in 1.8 mls DMSO in a vial, for use as a calibration solution. Both solutions are stirred for 24 hours at 25° C. The saturated aqueous solution and DMSO calibration solution are then transferred into deep 96-well plates. The saturated buffer solution plate is centrifuged at a relative centrifugal force of 4310 g and then the aqueous supernatant is transferred into a second deep well plate and centrifuged. After a further transfer of the aqueous supernatant and 50% dilution with buffer, the final sample plate and DMSO calibration plate are analysed using HPLC-UV-MS. Quantification of the sample solubility is by comparison of sample and calibration UK peak areas at 250 nm (alternative wavelength selected if 250 nm is unsuitable) with MS confirmation of the compound Id.

f) Assessment of Aqueous Solubility in Buffers and Simulated Intestinal Fluid.

Solubility is tested in the following medium at the specified temperatures:

*Simulated Intestinal Fluid (Fasted) FaSSIF* (*Galia and Dressman et al, Pharms Res*, 15(5), 1998, p 698).
Sodium Taurocholate (3 mM); Egg Lecithin (0.75 mM); $KH_2PO_4$ (0.03 M); KCl (0.1 M);
NaOH (to adjust to pH 6.5). Measured at 37° C.

*Sørensen's Phosphate Buffer* (*Handbook of Biochemistry*, pg. 234-237).
Solution A 0.067 M Monopotassium phosphate
Solution B 0.067 M Disodium phosphate
Measured at 25° C. and 37° C.

Appropriate quantities (determined from solubility test (f) above and/or predicted pH solubility curve) of the compound under investigation are accurately weighed in duplicate into 2-dram glass vials.

To each set of replicate vials, a minimum of 1.50 ml of the appropriate medium which is added pH 6.8 Sørensen's Phosphate Buffer or FaSSIF. All weighings must be sufficient to saturate the medium in each case.

A PTFE coated magnetic follower is added to each vial before they are sealed and placed on a Variomag magnetic reaction stirrer block (CanLab). The stirrer blocks are maintained at the appropriate temperature (see above), covered in aluminium foil to reduce exposure to light and stirred in alternate directions at 800 r.p.m.

Each vial is sampled at the prescribed time point for the media being tested. Firstly the pH and then the active content in each sample is determined at each time point in the following way.

pH

Using a suitable pH meter (Hydrus 400-Fisher), electrode and standard pH buffers, calibrate the instrument at pH 4.01 and 7.00 at ambient temperature.

By placing the electrode in each replicate sample, determine the pH at ambient temperature and report the result to one decimal place. The electrode is rinsed with de-ionised water and wiped dry between determinations.

Active Content by HPLC

From each sample, a 0.4 ml aliquot is transferred to a polycarbonate ultracentrifuge tube (Beckman). The samples are spun at 40 000 r.p.m. for 15 minutes at the appropriate temperature for the media being tested using the TL Optima Ultracentrifuge (Beckman). The supernatant from each ultracentrifuge tube is transferred to a second ultracentrifuge tube and spun once more under the same conditions.

The supernatant from each sample is analysed under the optimised HPLC method for the compound under investigation and the active content determined against an external standard. The supernatant may require diluting with a suitable solvent to bring the concentration within the linear range of the HPLC method. This can normally be estimated from the aqueous predicted pH solubility curve and in the case of the co-solvents from the amount of compound that has been added.

Although the pharmacological properties of the compounds of the Formula I vary with structural change as expected, in general activity possessed by compounds of the Formula I, may be demonstrated at the following concentrations or doses in one or more of the above tests (a), (b), (c) or (d):—

| | |
|---|---|
| Test (a):- | $IC_{50}$ in the range, for example, 100 nM or less; |
| Test (b):- | $IC_{50}$ in the range, for example, 1 µM or less; |
| Test (c):- | $IC_{50}$ in the range, for example, 1 µM or less; |
| Test (d):- | $IC_{50}$ of, for example, greater than 30 µM. |

By way of example, using Test (a) for the inhibition of HDAC1 and Test (b) for the inhibition of proliferation in whole cells, the compound described in Example 4 herein gave the $IC_{50}$ results shown below in Table A below. The table also includes the corresponding result for N-(2-aminophenyl)-4-(1-(pyrid-2-ylmethyl)piperidin-4-yl)benzamide (Compound [1] above):

TABLE A

| Compound of Example | $IC_{50}$ Test (a) (In vitro assay for the inhibition of HDAC1) | $IC_{50}$ Test (b) (In vitro assay for the inhibition of whole cell proliferation) |
|---|---|---|
| 4 | 0.081 µM | 0.508 µM |
| Comparative Compound 1 | 0.1 µM | 1.433 µM |

No physiologically unacceptable toxicity was observed in Test (d) at the effective dose for compounds tested of the present invention. Accordingly no untoward toxicological effects are expected when a compound of Formula I, or a pharmaceutically-acceptable salt thereof, is administered at the dosage ranges defined hereinafter.

In addition, although the solubility of the compounds of formula I will inevitably vary with structural change as expected, the compounds of formula I, in general, possess a solubility measured by test (e) above of, for example, greater than 100 µM.

According to a further aspect of the invention there is provided a pharmaceutical composition, which comprises a compound of the formula (I), or a pharmaceutically acceptable salt or pro-drug thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 μm or much less preferably 5 μm or less and more preferably between 5 μm and 1 μm, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

In general the above compositions may be prepared in a conventional manner using conventional excipients.

The compound of formula (I) will normally be administered to a warm-blooded animal at a unit dose within the range 5-5000 mg/m$^2$ body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

We have found that the compounds defined in the present invention, or a pharmaceutically acceptable salt thereof, are effective cell cycle inhibitors (anti-cell proliferation agents), and this property is believed to arise from their HDAC inhibitory activity. We also believe that the compounds of the present invention may be involved in the inhibition of angiogenesis, activation of apoptosis and differentiation. Accordingly the compounds of the present invention are expected to be useful in the treatment of diseases or medical conditions mediated alone or in part by HDAC enzymes, i.e. the compounds may be used to produce a HDAC inhibitory effect in a warm-blooded animal in need of such treatment. Thus, the compounds of the present invention provide a method for treating the proliferation of malignant cells characterised by inhibition of HDAC enzymes, i.e. the compounds may be used to produce an anti-proliferative effect mediated alone or in part by the inhibition of HDACs.

According to another aspect of the present invention there is provided a compound of the formula (I), or a pharmaceutically acceptable salt or pro-drug thereof, as defined hereinbefore for use in a method of treatment of the human or animal body by therapy.

Thus according to a further aspect of the invention there is provided a compound of the formula (I), or a pharmaceutically acceptable salt or pro-drug thereof, as defined hereinbefore for use as a medicament.

According to a further aspect of the invention there is provided the use of a compound of the formula (I), or a pharmaceutically acceptable salt or pro-drug thereof, as defined hereinbefore in the manufacture of a medicament for use in the production of a HDAC inhibitory effect in a warm-blooded animal such as man.

According to a further feature of this aspect of the invention there is provided a method for producing a HDAC inhibitory effect in a warm-blooded animal, such as man, in need of such treatment which comprises administering to said animal an effective amount of a compound of the formula (I), or a pharmaceutically acceptable salt or pro-drug thereof, as defined hereinbefore.

According to a further aspect of the invention there is provided the use of a compound of the formula (I), or a pharmaceutically acceptable salt or pro-drug thereof, as defined hereinbefore in the manufacture of a medicament for use in the production of a cell cycle inhibitory (anti-cell-proliferation) effect in a warm-blooded animal such as man.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of the formula (I), or a pharmaceutically acceptable salt or pro-drug thereof, as defined hereinbefore.

According to an additional feature of this aspect of the invention there is provided a method of treating cancer in a warm-blooded animal, such as man, in need of such treatment which comprises administering to said animal an effective amount of a compound of the formula (I), or a pharmaceutically acceptable salt or pro-drug thereof, as defined hereinbefore.

According to a further feature of the invention there is provided a compound of the formula (I), or a pharmaceutically acceptable salt or pro-drug thereof, as defined hereinbefore in the manufacture of a medicament for use in the treatment of cancer. According to an additional feature of this aspect of the invention there is provided a compound of the formula (I), or a pharmaceutically acceptable salt or pro-drug thereof, as defined hereinbefore, for use in the treatment of cancer.

According to an additional feature of this aspect of the invention there is provided the use of a compound of the formula (I), or a pharmaceutically acceptable salt or pro-drug thereof, as defined hereinbefore, for use in the manufacture of a medicament for the treatment of cancer.

In a further aspect of the present invention there is provided the use of a compound of the formula (I), or a pharmaceutically acceptable salt or pro-drug thereof, as defined hereinbefore, in the manufacture of a medicament for use in lung cancer, colorectal cancer, breast cancer, prostate cancer, lymphoma and/or leukaemia.

In a further aspect of the present invention there is provided a method of treating lung cancer, colorectal cancer, breast cancer, prostate cancer, lymphoma or leukaemia, in a warm-blooded animal, such as man, in need of such treatment which comprises administering to said animal an effective amount of a compound of the formula (I), or a pharmaceutically acceptable salt or pro-drug thereof, as defined hereinbefore.

Cancers that are amenable to treatment with the present invention include oesophageal cancer, myeloma, hepatocellular, pancreatic and cervical cancer, Ewings tumour, neuroblastoma, kaposis sarcoma, ovarian cancer, breast cancer, colorectal cancer, prostate cancer, bladder cancer, melanoma, lung cancer [including non small cell lung cancer (NSCLC) and small cell lung cancer (SCLC)], gastric cancer, head and neck cancer, brain cancer, renal cancer, lymphoma and leukaemia.

The HDAC inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(x) cell cycle inhibitors including for example CDK inhibitiors (eg flavopiridol) and other inhibitors of cell cycle checkpoints (eg checkpoint kinase); inhibitors of aurora kinase and other kinases involved in mitosis and cytokinesis regulation (eg mitotic kinesins); and other histone deacetylase inhibitors; and (xi) differentiation agents (for example retinoic acid and vitamin D).

According to this aspect of the invention there is provided a pharmaceutical composition comprising a compound of the formula (I) as defined hereinbefore and an additional antitumour substance as defined hereinbefore for the conjoint treatment of cancer.

There is further provided is a compound of the formula (I), or a pharmaceutically acceptable salt or pro-drug thereof, as defined hereinbefore, for use in a method of treating inflammatory diseases, autoimmune diseases and allergic/atopic diseases.

In particular a compound of the formula (I), or a pharmaceutically acceptable salt thereof, as defined hereinbefore, is provided for use in a method of treating inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis), multiple sclerosis, atherosclerosis, spondyloarthropathies (ankylosing spondylitis, psoriatic arthritis, arthritis connected to ulcerative colitis), AIDS-related neuropathies, systemic lupus erythematosus, asthma, chronic obstructive lung diseases, bronchitis, pleuritis, adult respiratory distress syndrome, sepsis, and acute and chronic hepatitis (either viral, bacterial or toxic).

Further provided is a compound of the formula (I), or a pharmaceutically acceptable salt or pro-drug thereof, as defined hereinbefore, for use as a medicament in the treatment of inflammatory diseases, autoimmune diseases and allergic/atopic diseases in a warm-blooded animal such as man.

In particular a compound of the formula (I), or a pharmaceutically acceptable salt or pro-drug thereof, as defined hereinbefore, is provided for use as a medicament in the treatment of inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis), multiple sclerosis, atherosclerosis, spondyloarthropathies (ankylosing spondylitis, psoriatic arthritis, arthritis connected to ulcerative colitis), AIDS-related neuropathies, systemic lupus erythematosus, asthma, chronic obstructive lung diseases, bronchitis, pleuritis, adult respiratory distress syndrome, sepsis, and acute and chronic hepatitis (either viral, bacterial or toxic).

Further provided is the use of a compound of the formula (I), or a pharmaceutically acceptable salt thereof, as defined hereinbefore, in the manufacture of a medicament for use in the treatment of inflammatory diseases, autoimmune diseases and allergic/atopic diseases in a warm-blooded animal such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

In addition to their use in therapeutic medicine, the compounds of formula (I) and their pharmaceutically acceptable salts thereof, are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or using proprietory pre-packed normal phase silica cartridges, for example Redisep™ disposable chromatography cartridges obtained from Presearch Ltd., Hitchin, UK, or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the structures of the end-products of the Formula (I) were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale proton magnetic resonance spectra were determined using a Jeol JNM EX 400 spectrometer operating at a field strength of 400 MHz, Varian Gemini 2000 spectrometer operating at a field strength of 300 MHz, Bruker DPX-400 operating at 400 MHz or a Bruker AM300 spectrometer operating at a field strength of 300 MHz—measurements were taken at ambient temperature unless otherwise specified;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the formula (I) were determined after crystallisation from a conventional organic solvent such as ethanol, methanol, acetone, ether or hexane, alone or in admixture;

(viii) the following abbreviations have been used:—
DMSO dimethylsulphoxide
THF tetrahydrofuran
DIPEA N,N-diisopropylethylamine
IPA isopropylalcohol
Boc/BOC tert butyloxycarbonyl
HCl hydrochloric acid
Cbz/CBZ benzyloxycarbonyl
Tf trifluoromethylsulphonyl
LiHMDS lithium hexamethyldisilazide
N-phenyl-bis(trifluoromethanesulfonimide)
DME 1,2-dimethoxyethane
CDMT 2-chloro-4,6-dimethoxy-1,3,5-triazine

EXAMPLE 1

N-(2-Aminophenyl)-4-{1-[(1-methyl-1H-pyrazol-4-yl)methyl]piperidin-4-yl}benzamide

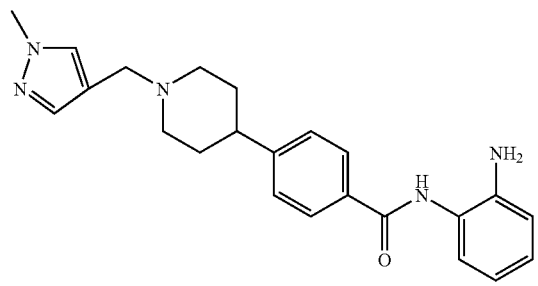

To a reaction vessel charged with 1-methyl-1H-pyrazole-4-carboxaldehyde (84.5 mg, 0.77 mmol) was added a solution of tert-butyl 2-[(4-piperidin-4-ylbenzoyl)amino]phenylcarbamate (prepared as described in Method 1 below; 300 mg, 0.76 mmol) in dichloromethane (7 ml) and N,N-dimethylformamide (0.5 ml). tert-Butyl 2-[(4-piperidin-4-ylbenzoyl)amino]phenylcarbamate may also be prepared according to the process described in Method 4 below. Acetic acid (50 µl, 0.87 mmol) was added and the reaction mixture allowed to stir at ambient temperature for 45 minutes. Sodium triacetoxyborohydride (250 mg, 1.18 mmol) was then added and reactions allowed to stir for a further 76 hours, before being diluted with methanol and poured directly onto an SCX-2 cartridge (10 g). The cartridge was washed through with methanol (80 ml) before eluting the products with a 2M solution of ammonia in methanol (50 ml). The relevant fractions were evaporated to dryness and the resultant residue redissolved in dichloromethane (3 ml) and treated with trifluoroacetic acid (1 ml). This mixture was stirred at ambient temperature for 2 hours before diluting with dichloromethane and pouring onto an SCX-2 cartridge (5 g). The cartridge was washed with methanol (20 ml) then products eluted with a 2M solution of ammonia in methanol (20 ml). The ammoniacal fraction was evaporated to dryness and the resultant residue was purified by flash chromatography on silica, eluting with 10% methanol in dichloromethane, to afford the title compound (117 mg, 40%); NMR Spectrum: (DMSO $d_6$) δ 1.70 (m, 4H), 2.01 (t, 2H), 2.57 (m, 1H), 2.95 (m, 2H), 3.38 (s, 2H), 3.81 (s, 3H), 4.86 (s, 2H), 6.60 (m, 1H), 6.78 (m, 1H), 6.97 (m, 1H), 7.18 (m, 1H), 7.31 (s, 1H), 7.37 (d, 2H), 7.57 (s, 1H), 7.91 (d, 2H), 9.56 (s, 1H); Mass Spectrum: M+H$^+$390.

EXAMPLE 2

Using an analogous procedure to that described in Example 1, tert-butyl 2-[(4-piperidin-4-ylbenzoyl)amino] phenylcarbamate was reacted with the appropriate pyrazole-carbaldehyde starting material (SM) to give the compounds described in Table 1

TABLE 1

| Example | R | Analytical Data | SM |
|---|---|---|---|
| 2A | (3-methyl-1-methyl-1H-pyrazol-4-yl)methyl group | NMR Spectrum: (CDCl₃) δ 1.81 (m, 4 H), 2.07 (m, 2 H), 2.25 (s, 3 H), 2.56 (m, 1 H), 3.04 (m, 2 H), 3.39 (s, 2 H), 3.81 (s, 3 H), 3.85 (s, 2 H), 6.84 (m, 2 H), 7.08 (m, 1 H), 7.24 (s, 1 H), 7.33 (m, 3 H), 7.82 (m, 3 H). Mass Spectrum: M + Na⁺ 426. | Commercially available |
| 2B | (3-methyl-1-methyl-1H-pyrazol-5-yl)methyl group | NMR Spectrum: (DMSO d₆) δ 1.67 (m, 2 H), 1.78 (m, 2 H), 2.08 (m, 5 H), 2.59 (m, 1 H), 2.93 (m, 2 H), 3.48 (s, 2 H), 3.74 (s, 3 H), 4.86 (s, 2 H), 5.92 (s, 1 H), 6.60 (m, 1 H), 6.78 (m, 1 H), 6.97 (m, 1 H), 7.17 (m, 1 H), 7.38 (d, 2 H), 7.91 (d, 2 H), 9.56 (s, 1 H); Mass Spectrum: M + Na⁺ 426. | Commercially available |

EXAMPLE 3

N-(2-Aminophenyl)-4-[1-(1H-pyrazol-3-ylmethyl) piperidin-4-yl]benzamide

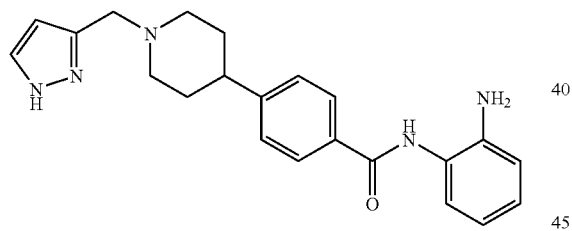

tert-Butyl 2-[(4-piperidin-4-ylbenzoyl)amino]phenylcarbamate (prepared as described in Method 1 below; 200 mg, 0.51 mmol) and 1H-pyrazole-3-carbaldehyde (50.7 mg, 0.53 mmol) were stirred at ambient temperature in dichloromethane (5 ml) for 1 hour. Sodium triacetoxyborohydride (150 mg, 0.71 mmol) was added and the mixture stirred at ambient temperature for 48 hours. The resulting solution was absorbed onto an SCX-2 column, which was washed with methanol (2 column volumes) and then the product eluted with a 2M solution of ammonia in methanol (2 column volumes) to give a foam. This was dissolved in 1,4-dioxane (2 ml), a 4M solution of hydrogen chloride in 1,4-dioxane (2 ml) was added and the solution stirred at ambient temperature for 48 hours. The product was filtered and washed with diethyl ether and air-dried. The resulting solid was dissolved in water, basified with 2N sodium hydroxide and the resulting solid filtered, washed with water and dried under vacuum to give the title compound (61 mg, 44%). NMR Spectrum: ¹H NMR (DMSO d₆) δ 1.71 (m, 4H), 2.07 (m, 2H), 2.56 (m, 1H), 2.95 (m, 2H), 3.53 (s, 2H), 4.86 (s, 2H), 6.16 (s, 1H), 6.60 (m, 1H), 6.78 (d, 1H), 6.97 (t, 1H), 7.18 (d, 1H), 7.37 (d, 2H), 7.64 (m, 1H), 7.91 (d, 2H), 9.55 (s, 1H), 12.59 (m, 1H); Mass Spectrum: M+H⁺ 376.

EXAMPLE 4

N-(2-Aminophenyl)-4-{1-[(5-methoxy-1,3-dimethyl-1H-pyrazol-4-yl)methyl]piperidin-4-yl}benzamide

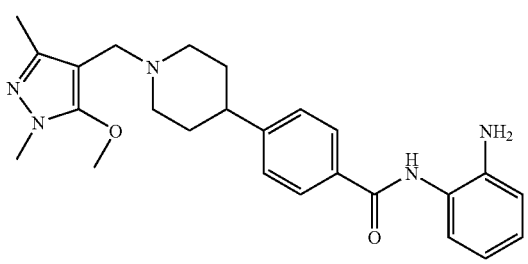

Using an analogous procedure to that described in Example 3, tert-butyl 2-[(4-piperidin-4-ylbenzoyl)amino] phenylcarbamate (prepared as described in Method 1 below; 200 mg, 0.51 mmol) was reacted with 5-methoxy-1,3-dimethyl-1H-pyrazole-4-carbaldehyde (92.6 mg, 0.60 mmol) to give the title compound (68 mg, 36%); NMR Spectrum: (DMSO d₆) δ 1.63 (m, 2H), 1.78 (m, 2H), 2.00 (m, 2H), 2.06 (s, 3H), 2.57 (m, 1H), 2.94 (m, 2H), 3.25 (s, 2H), 3.50 (s, 3H), 3.99 (s, 3H), 4.86 (br s, 2H), 6.60 (m, 1H), 6.78 (d, 1H), 6.97 (m, 1H), 7.17 (d, 1H), 7.37 (d, 2H), 7.91 (d, 2H), 9.55 (s, 1H); Mass Spectrum: M+H⁺434.

EXAMPLE 5

N-(2-Aminophenyl)-4-{1-[(3-ethyl-1H-pyrazol-4-yl)methyl]piperidin-4-yl}benzamide

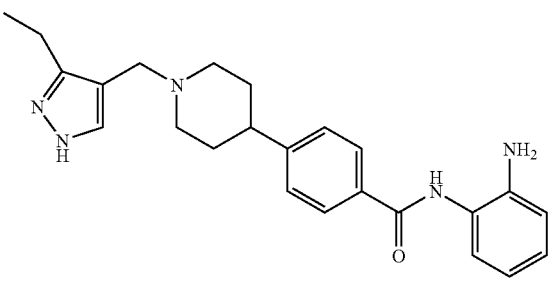

tert-Butyl 2-[(4-piperidin-4-ylbenzoyl)amino]phenylcarbamate (prepared as described in Method 1 below; 395 mg, 1.0 mmol) and 3-ethyl-1H-pyrazole-4-carbaldehyde (149 mg, 1.2 mmol) were stirred at ambient temperature in dichloromethane (10 ml) for 1 hour. Sodium triacetoxyborohydride (297 mg, 1.4 mmol) was added and the mixture stirred at ambient temperature for 24 hours. The resulting solution was absorbed onto an SCX-2 column which was washed with methanol (2 column volumes) and then the product eluted with a 2M solution of ammonia in methanol (2 column volumes) to give the product as a white foam. This was purified by chromatography on silica eluting with 10% methanol in dichloromethane. The residue was dissolved in dichloromethane (4 ml) and trifluoroacetic acid (1 ml) was added and the mixture stirred for 3 hours at ambient temperature. The resulting solution was absorbed onto an SCX-2 column which was washed with methanol (2 column volumes) and then the product eluted with a 2M solution of ammonia in methanol (2 column volumes) to give the title compound (232 mg, 75%). NMR Spectrum: (DMSO $d_6$) δ 1.18 (t, 3H), 1.65 (m, 2H), 1.77 (m, 2H), 2.00 (m, 2H), 2.57 (m, 3H), 2.95 (m, 2H), 3.34 (s, 2H), 4.86 (br s, 2H), 6.60 (m, 1H), 6.78 (d, 1H), 6.97 (m, 1H), 7.17 (d, 1H), 7.29 (br s, 1H), 7.37 (d, 2H), 7.91 (d, 2H), 9.55 (s, 1H), 12.39 (s, 1H); Mass Spectrum: M+H$^+$ 404.

EXAMPLE 6

N-(2-Aminophenyl)-4-{1-[(1,3,5-trimethyl-1H-pyrazol-4-yl)methyl]piperidin-4-yl}benzamide

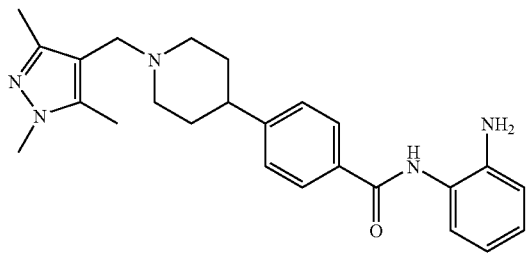

Using an analogous procedure to that described in Example 5, tert-butyl 2-[(4-piperidin-4-ylbenzoyl)amino]phenylcarbamate (prepared as described in Method 1 below; 200 mg, 0.51 mmol) was reacted with 1,3,5-trimethyl-1H-pyrazole-4-carbaldehyde (83.5 mg, 0.60 mmol) to give the title compound (70 mg, 56%); NMR Spectrum: (DMSO d6) δ 1.65 (m, 2H), 1.77 (m, 2H), 1.98 (m, 2H), 2.09 (s, 3H), 2.18 (s, 3H), 2.57 (m, 1H), 2.92 (m, 2H), 3.24 (s, 2H), 3.63 (s, 3H), 4.86 (br s, 2H), 6.60 (m, 1H), 6.78 (d, 1H), 6.97 (m, 1H), 7.17 (d, 1H), 7.37 (d, 2H), 7.91 (d, 2H), 9.55 (s, 1H); Mass Spectrum: M+H$^+$418.

EXAMPLE 7A

N-(2-Aminophenyl)-4-{1-[(1,3-dimethyl-1H-pyrazol-4-yl)methyl]piperidin-4-yl}benzamide

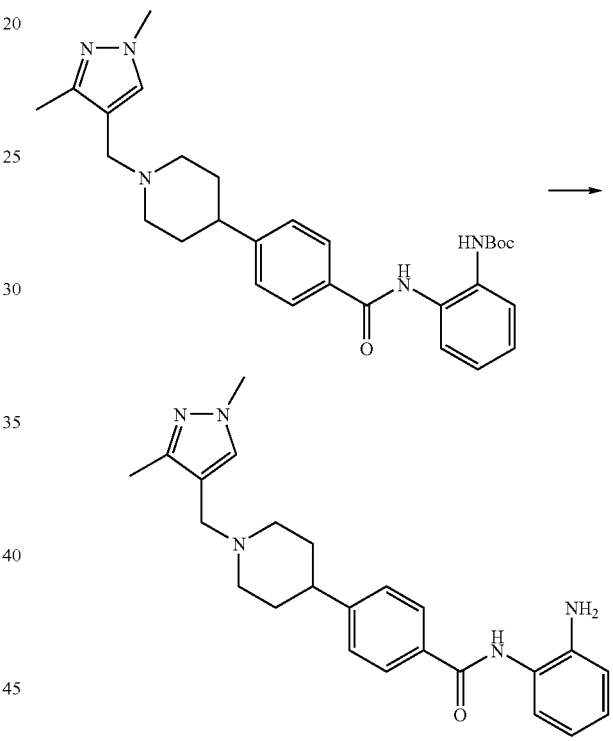

tert-Butyl (2-{[4-(1-{1,3-dimethyl-1H-pyrazol-4-ylmethyl}piperidin-4-yl)benzoyl]amino}phenyl)carbamate (prepared as described in Method 6 below; 7.61 g, 15.11 mmol) was dissolved in 1,4 dioxane (70 ml) and cooled to 0° C., using an ice-water bath. A 4M solution of hydrogen chloride in 1,4 dioxane (150 ml, 600 mmol) was then added slowly. The resultant suspension was allowed to warm to room temperature and lumps broken up by agitation with a glass rod. The reaction mixture was stirred at room temperature for 18 hours. The mixture was filtered, under suction. The solid obtained was dissolved in water (200 ml), and the solution adjusted to pH 12 by slow addition of a 2M aqueous solution of sodium hydroxide. The mixture obtained was extracted with dichloromethane (300 ml) and the organics separated. The aqueous phase was further extracted with dichloromethane (200 ml) and the combined extracts washed with brine, dried over magnesium sulphate, filtered and evaporated to give a clear gum. The gum was taken up in diethyl ether and re-evaporated to dryness to afford the title compound (5.69 g, 93%); NMR Spectrum (CDCl$_3$) δ 1.81 (m, 4H), 2.07 (m, 2H), 2.25 (s, 3H), 2.56 (m, 1H), 3.04 (m, 2H), 3.39 (s, 2H), 3.81 (s, 3H), 3.85 (s, 2H), 6.84 (m, 2H), 7.08 (m, 1H), 7.24 (s, 1H), 7.33 (m, 3H), 7.82 (m, 3H).

Mass Spectrum: M+H$^+$404.

EXAMPLE 7B

N-(2-Aminophenyl)-4-{1-[(1,3-dimethyl-1H-pyrazol-4-yl)methyl]piperidin-4-yl}benzamide tert-Butyl (2-{[4-(1-{1,3-dimethyl-1H-pyrazol-4-ylmethyl}piperidin-4-yl)benzoyl]amino}phenyl)carbamate (Method 6 below; 92.3 g, 183.3 mmol) was slurried in methanol (754 ml) and water (141 ml) and cooled to 0-5° C. Concentrated hydrochloric acid was added maintaining the temperature below 20° C. The reaction mixture was stirred for 20 hours at ambient temperature. The reaction was cooled to 0-5° C. and aqueous sodium hydroxide solution added maintaining the temperature at below 20° C. until a pH of 12-14 is obtained. The reaction mixture was heated to reflux temperature for 30 minutes before cooling to 20° C. over about 4 hours. The product was collected by filtration and washed with aqueous methanol before being dried in vacuo at 45° C. to constant weight to give the title compound (63.3 g 86%).

NMR Spectrum (DMSO d$_6$), 1.65 (m, 2H), 1.73 (m, 2H), 1.96 (t, 2H), 2.08 (s, 3H), 2.55 (m, 1H), 2.92 (d, 2H), 3.28 (s, 2H), 3.75 (s, 3H), 4.87 (s, 2H), 6.59 (m, 1H), 6.77 (m, 1H), 6.96 (m, 1H), 7.2 (d, 1H), 7.35 (d, 2H), 7.44 (s, 1H), 7.90 (d, 2H), 9.56 (s, 1H).

Mass Spectrum: M+H$^+$404.

EXAMPLE 8

N-(2-Aminophenyl)-4-{1-[(1,5-dimethyl-1H-pyrazol-4-yl)methyl]piperidin-4-yl}benzamide

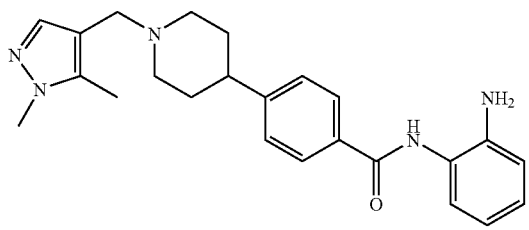

tert-Butyl {2-[(4-{1-[(1,5-dimethyl-1H-pyrazol-4-yl)methyl]piperidin-4-yl}benzoyl)amino]phenyl}carbamate (prepared as described in Method 7; 308 mg, 0.61 mmol) was taken up in dichloromethane (2 ml) and trifluoroacetic acid (1 ml) added. The reaction mixture was stirred at ambient temperature for 1 hour before being poured onto an SCX-3 cartridge (5 g). The cartridge was washed with dichloromethane (50 ml) and methanol (50 ml), before eluting the product with a 2M solution of ammonia in methanol (50 ml). The ammoniacal fraction was evaporated to afford a white solid (182 mg) that was purified by reverse phase preparative HPLC to afford the title compound (134 mg, 55%); NMR Spectrum: (DMSO d$_6$) δ 1.70 (m, 4H), 2.01 (m, 2H), 2.22 (s, 3H), 2.57 (m, 1H), 2.95 (m, 2H), 3.28 (s, 2H), 3.71 (s, 3H), 4.86 (s, 2H), 6.60 (m, 1H), 6.78 (m, 1H), 6.97 (m, 1H), 7.17 (m, 1H), 7.23 (s, 1H), 7.37 (d, 2H), 7.90 (d, 2H), 9.55 (s, 1H); Mass Spectrum: M+H$^+$404.

EXAMPLE 9

N-(2-Aminophenyl)-4-{1-[(1-ethyl-5-methyl-1H-pyrazol-4-yl)methyl]piperidin-4-yl}benzamide

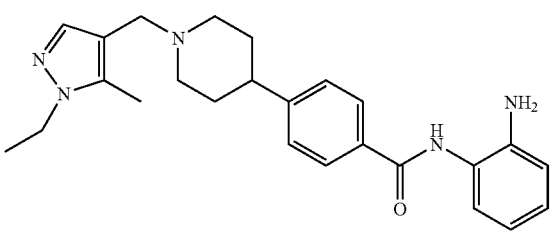

A solution of 1-ethyl-5-methyl-1H-pyrazole-4-carbaldehyde (141 mg, 1.02 mmol) in dichloromethane (1 ml) was added to a solution of tert-butyl 2-[(4-piperidin-4-ylbenzoyl)amino]phenylcarbamate (prepared as described in Method 1 below; 300 mg, 0.76 mmol) in dichloromethane (6.5 ml). Acetic acid (45 μl, 0.79 mmol) was added and reaction mixture stirred for 4 hours. N,N-dimethylformamide (1 ml) was then added and stirring continued for a further 30 minutes before addition of sodium triacetoxyborohydride (245 mg, 1.16 mmol) as a solid. The reaction mixture was then allowed to stir at ambient temperature for 18 hours (overnight). The reaction mixture was diluted to double volume by addition of methanol and poured directly onto a pre-washed (with methanol) SCX-2 cartridge (10 g). Cartridge was washed with methanol (60 ml) before eluting products with a 2M ammonia solution in methanol (50 ml). The ammoniacal eluant was evaporated to give a colourless gum (420 mg), which was taken up in dichloromethane (5 ml) and treated with trifluoroacetic acid (2 ml). The mixture was allowed to stir for 2 hours before diluting with dichlormethane (10 ml) and pouring onto a pre-washed (with methanol) SCX-2 cartridge (10 g). The cartridge was washed through with dichloromethane (40 ml), methanol (50 ml) and then products eluted with a 2M solution of ammonia in methanol (50 ml). Evaporation of the ammoniacal fraction afforded a pale yellow gum (300 mg), which was purified by reverse phase preparative HPLC to afford the title compound (172 mg, 54%); NMR Spectrum: (DMSO d$_6$) δ 1.27 (t, 3H), 1.66 (m, 4H), 1.98 (m, 2H), 2.21 (s, 3H), 2.56 (m, 1H), 2.92 (m, 2H), 3.29 (s, 2H), 4.02 (q, 2H), 4.85 (s, 2H), 6.59 (m, 1H), 6.77 (m, 1H), 6.95 (m, 1H), 7.16 (m, 1H), 7.23 (s, 1H), 7.35 (d, 2H), 7.89 (d, 2H), 9.54 (s, 1H); Mass Spectrum: M+H$^+$418.

EXAMPLES 10 AND 11

Using an analogous procedure to that described in Example 9, tert-butyl 2-[(4-piperidin-4-ylbenzoyl)amino]phenylcarbamate (prepared as described in Method 1 below) was reacted with the appropriate pyrazolecarbaldehyde starting material to give the compounds described in Table 2.

TABLE 2

[Structure: R-N(piperidine)-phenyl-C(O)NH-phenyl-NH2]

| Example | R | Analytical Data | SM |
|---|---|---|---|
| 10 | [pyrazole-CH2-C(Et)2-CH2- group with N-ethyl pyrazole] | NMR Spectrum: (DMSO d<sub>6</sub>) δ 1.35 (t, 3 H), 1.68 (m, 4 H), 1.99 (m, 2 H), 2.56 (m, 1 H), 2.94 (m, 2 H), 3.32 (s, 2 H), 4.08 (q, 2 H), 4.85 (s, 2 H), 6.58 (m, 1 H), 6.77 (m, 1 H), 6.95 (m, 1 H), 7.16 (m, 1 H), 7.31 (s, 1 H), 7.36 (d, 2 H), 7.60 (s, 1 H), 7.89 (d, 2 H), 9.54 (s, 1 H); Mass Spectrum: M + H$^+$ 404 | Commercially available |
| 11 | [3-methyl-1-ethyl pyrazole-CH2- group] | NMR Spectrum: (DMSO d$_6$) δ 1.32 (t, 3 H), 1.67 (m, 4 H), 1.98 (m, 2 H), 2.12 (s, 3 H), 2.56 (m, 1 H), 2.92 (m, 2 H), 3.28 (s, 2 H), 3.99 (q, 2 H), 4.85 (s, 2 H), 6.58 (m, 1 H), 6.77 (m, 1 H), 6.95 (m, 1 H), 7.16 (m, 1 H), 7.35 (d, 2 H), 7.47 (s, 1 H), 7.89 (d, 2 H), 9.54 (s, 1 H); Mass Spectrum: M + H$^+$ 418 | Commercially available |

Method Section—Preparation of Starting Materials
Method 1 tert-Butyl {2-[(4-piperidin-4-ylbenzoyl)amino]phenyl}carbamate

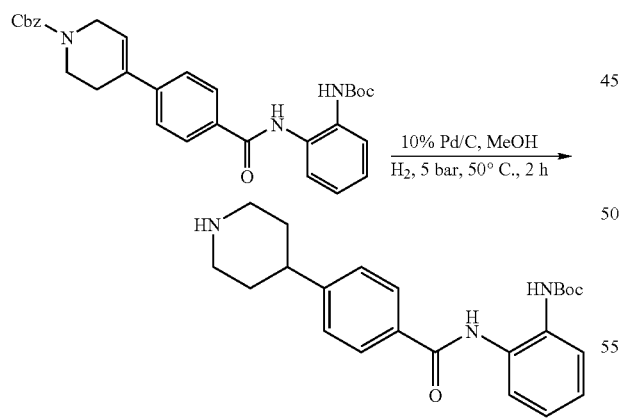

To a solution of benzyl 4-{4-[({2-[(tert-butoxycarbonyl)amino]phenyl}amino)carbonyl]phenyl}-3,6-dihydropyridine-1(2H)-carboxylate (269 g, 524 mmol; prepared as described in Method 2 below) in methanol (3000 ml) was added 10% palladium on charcoal (10 g). The reaction mixture was placed under 5 bar pressure of hydrogen gas and heated to 50° C. for 1 h. The reaction mixture was cooled to room temperature, filtered through a pad of celite and the solvent evaporated under reduced pressure. The resultant foam was triturated under diethyl ether and filtered to give a white solid. This product was ground finely and stirred with 95:5 diethyl ether/ethyl acetate then collected by suction filtration. This solid was washed with diethyl ether, isohexane and dried in vacuo to afford the title compound (167 g, 81%); NMR Spectrum: (DMSO-d$_6$) 1.45 (s, 9H), 1.57 (m, 2H), 1.72 (m, 2H), 2.61 (t, 2H), 2.69 (m, 1H), 3.07 (m, 2H), 7.18 (m, 2H), 7.40 (d, 2H), 7.53 (d, 2H), 7.91 (d, 2H), 8.70 (br s, 1H), 9.82 (br s, 1H); Mass Spectrum: M+H$^+$396.

Method 2

Benzyl 4-{4-[({2-[(tert-butoxycarbonyl)amino]phenyl}amino)carbonyl]phenyl}-3,6-dihydropyridine-1(2H)-carboxylate

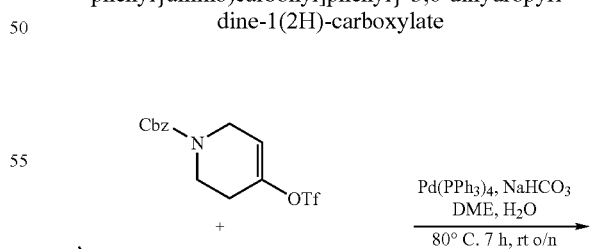

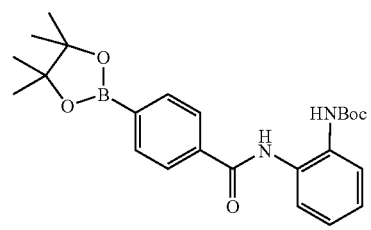

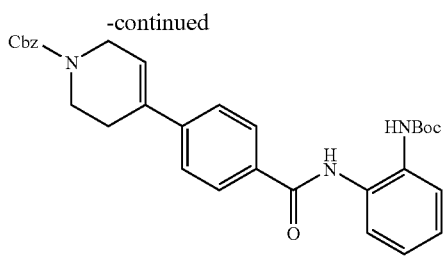

Tetrakis(triphenylphosphine)palladium(0) (8.0 g, 6.92 mmol) was added to a stirred suspension of N-(2-t-butoxycarbonylaminophenyl)-4-(4,4,5,5-tetramethyl-1,3,2,-dioxaborolan-2-yl)benzamide (288 g, 657 mmol; prepared as described in International Patent Publication number WO 03/087057, Method 13, page 60) and benzyl 4-{[(trifluoromethyl)sulfonyl]oxy}-3,6-dihydropyridine-1(2H)-carboxylate (240 g, 657 mmol; prepared as described in Method 3 below) in 1,2-dimethoxyethane (3000 ml) and saturated aqueous sodium bicarbonate solution (3000 ml). The reaction mixture was heated to 80° C. for 7 h, before being allowed to cool to ambient temperature, with stirring. The reaction mixture was then poured onto water (2000 ml) and extracted with ethyl acetate. The organic extracts were then dried over magnesium sulfate, filtered and evaporated to dryness to give the crude product as a grey solid. This was purified by flash column chromatography on silica, eluting with ethyl acetate/hexane (30:70 v/v) to afford the title compound (279 g, 82%); NMR Spectrum: (DMSO-$d_6$) δ 1.44 (s, 9H), 2.56 (m, 2H), 3.66 (m, 2H), 4.14 (m, 2H), 5.13 (s, 2H), 6.34 (m, 1H), 7.18 (m, 2H), 7.33 (m, 1H), 7.40 (m, 4H), 7.54 (m, 2H), 7.62 (d, 2H), 7.94 (d, 2H), 8.64 (br s, 1H), 9.81 (br s, 1H); Mass Spectrum: MNa$^+$ 550.

Method 3

Benzyl 4-{[(trifluoromethyl)sulfonyl]oxy}-3,6-dihydropyridine-1(2H)-carboxylate

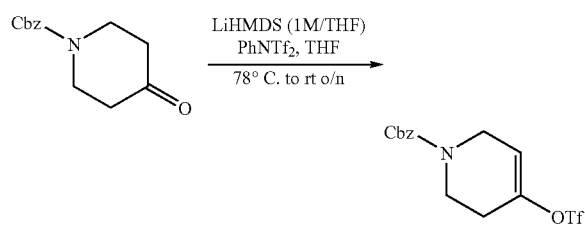

Benzyl 4-oxopiperidine-1-carboxylate (147 g, 630 mmol) was dissolved in tetrahydrofuran (500 ml), under an atmosphere of nitrogen. This solution was added, dropwise over 2 hours, to a stirred solution of lithium hexamethyldisilazide (20% solution in tetrahydrofuran, 556 ml, 662 mmol) under nitrogen maintaining the reaction temperature below −70° C. The reaction mixture was allowed to stir at −75° C. for a further 1 hour before dropwise addition over 2 hours, of a solution of N-phenyl-bis(trifluoromethanesulfonimide) (236 g, 661 mmol) in tetrahydrofuran (950 ml) again maintaining the reaction temperature below −70° C. The reaction was then allowed to warm to room temperature overnight followed by portionwise addition of 2M aqueous sodium hydroxide solution (800 ml). The layers were separated and the organic layer was washed with further 2M aqueous sodium hydroxide solution (600 ml), before evaporation to dryness. The resulting solid was dissolved in diethyl ether and washed with water. The organic layer was then filtered through celite, dried over sodium sulphate and evaporated to dryness to afford the title compound (140 g, 61%), which was taken through to the next stage without further purification.

Method 4 tert-butyl {2-[(4-piperidin-4-ylbenzoyl)amino]phenyl}carbamate (alternative method)

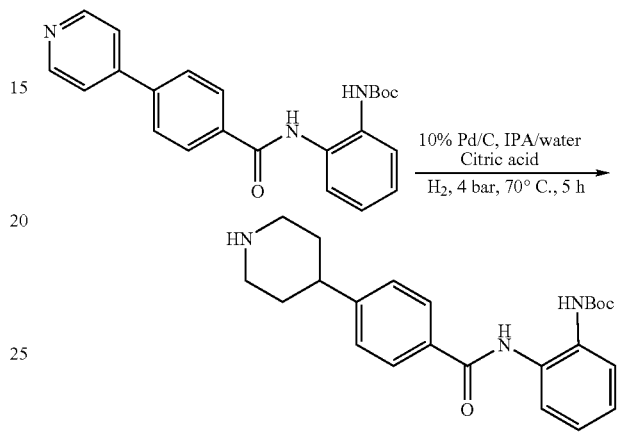

To tert-butyl {2-[4-pyrid-4-ylbenzoyl)amino]phenyl}carbamate (20 g, 51.35 mmol; prepared as described in Method 5A or 5B below), 10% palladium on charcoal (3.17 g) and citric acid (4.75 g, 24.65 mmol) was added water (80 ml) and IPA (80 ml). The reaction mixture was placed under 4 bar pressure of hydrogen gas and heated to 70° C. for 5 hours. The reaction mixture was cooled to 50° C. and filtered through a pad of Celite. The mixture was heated to 70° C. before 20% w/w aqueous sodium hydroxide solution was added (15 ml) over 10 minutes to pH 10-11. Further water (30 ml) was added then the mixture cooled to 40° C. over 1 hour, then re-heated to 60° C. for 30 minutes before cooling back to ambient temperature. The resultant precipitate was collected by filtration, washed with water (2×20 ml) and dried in vacuo, at 50° C., to afford the title compound (17.6 g, 84%);

NMR Spectrum: (DMSO-$d_6$) δ 1.45 (s, 9H), 1.53 (m, 2H), 1.70 (m, 2H), 2.58 (m, 1H), 2.66 (m, 2H), 3.03 (m, 2H), 3.31 (br s, 1H), 7.17 (m, 2H), 7.35 (d, 2H), 7.54 (m, 2H), 7.89 (d, 2H), 8.65 (br s, 1H), 9.75 (br s, 1H).

Mass Spectrum: M+H$^+$396.

Method 5A tert-Butyl {2-[4-pyrid-4-ylbenzoyl)amino]phenyl}carbamate

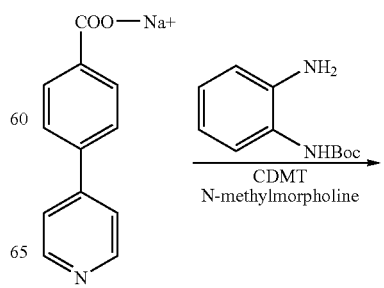

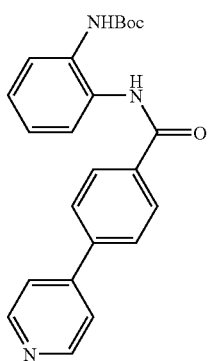

To sodium 4-(4-pyridyl)benzoate (55.2 g, 236.2 mmol), boc o-phenylene diamine (45.7 g. 217.6 mmol) and N-methylmorpholine (24 ml) in acetonitrile (300 ml) was added a screened solution of 2-chloro-4,6-dimethoxy-1,3,5-triazine (48.5 g, 270.5 mmol) in acetonitrile (152 ml) over 3 hours. The mixture was stirred for 22 hours before water (460 ml) was added. The resultant precipitate was collected by filtration, washed with 50% aqueous acetonitrile (3×100 ml) and dried in vacuo, at 50° C., to afford the title compound (75.6 g, 90%);

NMR Spectrum: (DMSO-$d_6$): δ1.45 (s, 9H), 7.17 (m, 2H), 7.56 (m, 2H), 7.81 (d, 2H), 7.99 (d, 2H), 8.11 (d, 2H), 8.69 (d, 2H), 9.94 (br s, 1H).

Mass Spectrum: M+H$^+$390.

Method 5B tert-Butyl {2-[4-pyrid-4-ylbenzoyl)amino]phenyl}carbamate

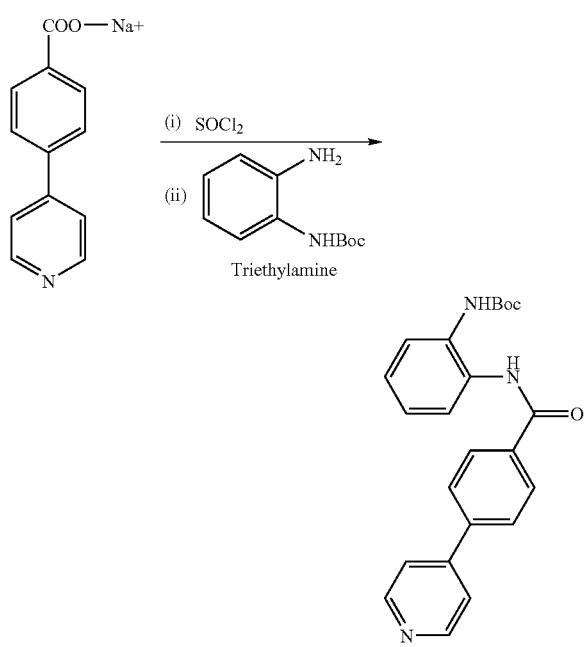

Sodium 4-(4-pyridyl)benzoate (10 g, 45.2 mmol) in acetonitrile (60 ml) was heated to 70° C. then thionyl chloride (6.6 ml, 90.4 mmol) was added. The reaction was heated at reflux temperature for 5 hours before being cooled to ambient temperature. Triethylamine (12.6 ml, 90.4 mmol) was added cautiously followed by a warmed solution of Boc o-phenylene diamine (9.42 g, 45.2 mmol) in acetonitrile (15 ml) being added over 10 minutes. A solution of sodium hydroxide (8.6 g, 109 mmol) in water (60 ml) was added and the resultant solid collected by filtration, washed with water (20 ml) and dried in vacuo, at 50° C., to afford the title compound (12.6 g, 68%).

NMR Spectrum: (DMSO-$d_6$): δ 1.45 (s, 9H), (7.17 (m, 2H), 7.56 (m, 2H), 7.81 (d, 2H), 7.99 (d, 2H), 8.11 (d, 2H) 8.69 (d, 2H), 9.94 (br s, 1H).

Mass Spectrum: M+H$^+$390.

Method 6A tert-Butyl (2-{[4-(1-{1,3-dimethyl-1H-pyrazol-4-ylmethyl}piperidin-4-yl)benzoyl]amino}phenyl)carbamate

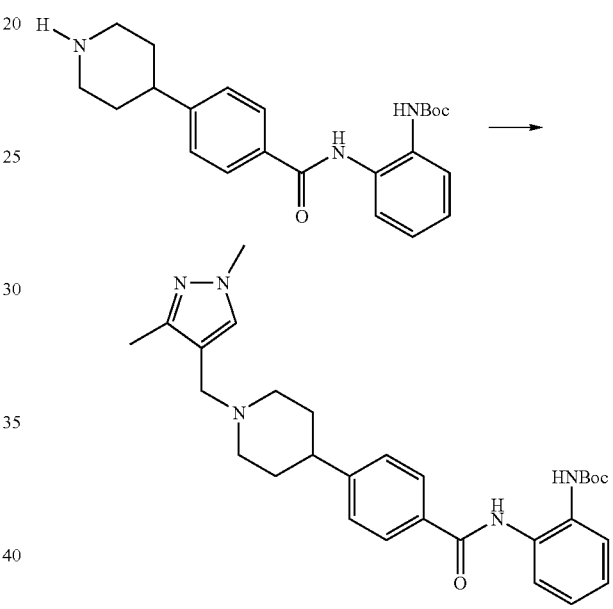

tert-Butyl 2-[(4-piperidin-4-ylbenzoyl)amino]phenylcarbamate (6.83 g, 17.3 mmol) and 1,3-dimethyl-1H-pyrazole-4-carbaldehyde (3.0 g, 24.2 mmol) were dissolved in dichloromethane (150 ml). Acetic acid (996 µl, 17.3 mmol) was then added and the reaction mixture allowed to stir at room temperature for four hours. Sodium triacetoxyborohydride (5.49 g, 25.9 mmol) was then added and reaction mixture stirred for a further 18 hours. Saturated aqueous sodium bicarbonate solution (300 ml) was then carefully added followed by dichloromethane (100 ml). The organic layer was separated and the aqueous layer re-extracted with more dichloromethane (150 ml). The combined organic extracts were dried over magnesium sulphate, filtered and evaporated to dryness. The residue obtained was purified by flash chromatography on silica, eluting with a 5% (v/v) solution of methanol in dichloromethane followed by a rising gradient of 5-10% (v/v) methanol in dichloromethane to afford a clear gum, which was taken up in diethyl ether and evaporated to dryness to afford the title compound (7.61 g, 87%); NMR Spectrum: (DMSO $d_6$) δ 1.43 (s, 9H), 1.69 (m, 4H), 1.98 (m, 2H), 2.10 (s, 3H), 2.56 (m, 1H), 2.92 (m, 2H), 3.26 (s, 2H), 3.70 (s, 3H), 7.15 (m, 2H), 7.40 (m, 3H), 7.52 (m, 2H), 7.87 (d, 2H), 8.60 (s, 1H), 9.73 (s, 1H); Mass Spectrum: M+H$^+$ 504.

Method 6B tert-Butyl (2-{[4-(1-{1,3-dimethyl-1H-pyrazol-4-ylmethyl}piperidin-4-yl)benzoyl]amino}phenyl)carbamate tert-Butyl 2-[(4-piperidin-4-ylbenzoyl)amino]phenylcarbamate (prepared as described in Method 4 above; 108.1 g, 273.3 mmol), 1,3-dimethyl-1H-pyrazole-4-carbaldehyde (35.6 g, 287 mmol) and palladium on charcoal (3.09 g, 1.37 mmol) were charged to a suitable pressure vessel. Tetrahydrofuran (920 ml), water (54 ml) and acetic acid (32.8 g, 546.7 mmol) charged and the stirred mixture heated to 60° C. under 3 bar of hydrogen until the reaction deemed complete. The mixture was then cooled to 40° C. and 2 M sodium hydroxide solution (410 ml, 820 mmol) added. On cooling to 25° C. the mixture was filtered to remove catalyst before tetrahydrofuran (650 ml) was added and the organic phase separated. The organic phase was partially concentrated by distillation before toluene (575 ml) was added. The distillation was continued whilst maintaining the reaction volume with further addition of toluene (690 ml). The reaction mixture was allowed to cool to ambient temperature over about 3 hours during which the product crystallizes. The solid was collected by filtration, washed with toluene (460 ml), then ethyl acetate (230 ml) before being dried in vacuo at 45° C. to constant weight to give the title compound (114.9 g, 83%).

Spectrum: (DMSO $d_6$), δ 1.434(s, 9H), 1.70 (m, 4H), 1.98 (m, 2H), 2.11 (s, 3H), 2.56 (m, 1H), 2.93 (m, 2H), 3.28 (s, 2H), 3.71 (s, 3H), 7.16 (m, 2H), 7.40 (m, 3H), 7.52 (m, 2H), 7.87 (d, 2H), 8.60 (s, 1H), 9.73 (s, 1H); Mass Spectrum: M+H$^+$ 504.

Method 7 tert-Butyl {2-[(4-{1-[(1,5-dimethyl-1H-pyrazol-4-yl)methyl]piperidin-4-yl}benzoyl)amino]phenyl}carbamate

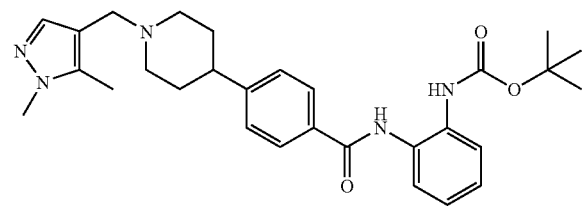

1,5-Dimethyl-1H-pyrazole-4-carbaldehyde (114 mg, 0.92 mmol) was added to a solution of tert-butyl 2-[(4-piperidin-4-ylbenzoyl)amino]phenylcarbamate (289 mg, 0.73 mmol) in dichloromethane (6 ml) followed by acetic acid (50 μl, 0.87 mmol). The reaction mixture was allowed to stir under nitrogen for 2.5 hours. Sodium triacetoxyborohydride (233 mg, 1.10 mmol) was added and the reaction mixture allowed to stir, at ambient temperature, for 18 hours (overnight). Saturated aqueous sodium bicarbonate solution (10 ml) was then added to the reaction and allowed to stir for 15 minutes. The organic phase was separated and the aqueous phase re-extracted with dichloromethane (10 ml). The combined organics were washed with water, dried over magnesium sulphate and evaporated to dryness to afford the product as a colourless gum (308 mg, 84%), which was used without further purification; Mass Spectrum: M+H$^+$504.

The invention claimed is:

1. A compound of formula (IA)

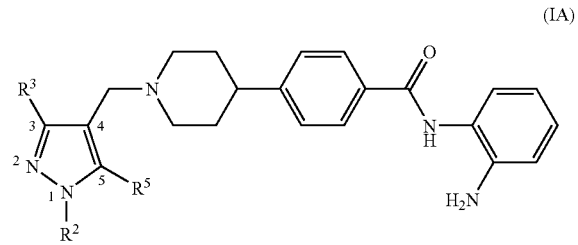

where $R^2$, $R^3$ and $R^5$ are each independently selected from hydrogen or methyl; or a pharmaceutically acceptable salt thereof.

2. A compound according to claim 1 wherein at least one group selected from $R^2$, $R^3$ and $R^5$ is other than hydrogen.

3. A compound according to claim 1 which is

N-(2-aminophenyl)-4-{1-[(1-methyl-1H-pyrazol-4-yl)methyl]piperidin-4-yl}benzamide, or a pharmaceutically acceptable salt thereof.

4. A compound according to claim 1 which is N-(2-aminophenyl)-4-{1-[(1,3-dimethyl-1H-pyrazol-4-yl)methyl]piperidin-4-yl}benzamide, or a pharmaceutically acceptable salt thereof.

5. A compound according to claim 1 which is N-(2-aminophenyl)-4-{1-[(1,3,5-trimethyl-1H-pyrazol-4-ylmethyl]piperidin-4-yl}benzamide, or a pharmaceutically acceptable salt thereof.

6. A compound according to claim 1 which is N-(2-Aminophenyl)-4-{1-[(1,5-dimethyl-1H-pyrazol-4-yl)methyl]piperidin-4-yl}benzamide, or a pharmaceutically acceptable salt thereof.

7. A pharmaceutical composition which comprises a compound according to claim 1, or a pharmaceutically acceptable salt thereof, in association with a pharmaceutically-acceptable diluent or carrier.

8. A process for preparing a compound as claimed in claim 1, or a pharmaceutically acceptable salt thereof, which process comprises either:

(a) the reaction of a compound of formula (II)

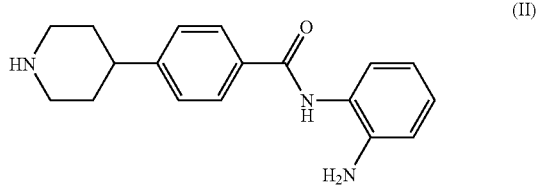

wherein the aniline moiety may be appropriately protected;

with a compound of the formula (III)

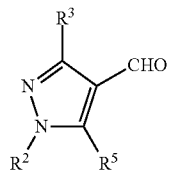
(III)

in the presence of a reducing agent, wherein $R^2$, $R^3$ and $R^5$ are as defined in claim 2; or (b) the reaction of a compound of formula (II) as defined above with a compound of formula (IV)

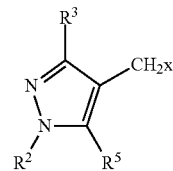
(IV)

in the presence of a suitable base;
wherein $R^2$, $R^3$ and $R^5$ are as defined in claim 2 and X is a reactive group;
and thereafter, if necessary, removing any residual protecting groups that may be present.

* * * * *